United States Patent
Kodama et al.

(10) Patent No.: US 8,278,303 B2
(45) Date of Patent: Oct. 2, 2012

(54) PHOSPHINE TRANSITION METAL COMPLEX, PROCESS FOR PRODUCING SAME, AND ANTICANCER AGENT

(75) Inventors: Hiroaki Kodama, Saga (JP); Keisuke Ohto, Saga (JP); Nobuhiko Oohara, Tokyo (JP); Kazuhiro Nakatsui, Tokyo (JP); Yoshirou Kaneda, Tokyo (JP)

(73) Assignee: Nippon Chemical Industrial Co., Ltd., Tokyo (JP)

( * ) Notice: Subject to any disclaimer, the term of this patent is extended or adjusted under 35 U.S.C. 154(b) by 699 days.

(21) Appl. No.: 12/302,517

(22) PCT Filed: May 31, 2007

(86) PCT No.: PCT/JP2007/061046
§ 371 (c)(1), (2), (4) Date: Jul. 22, 2009

(87) PCT Pub. No.: WO2007/139176
PCT Pub. Date: Dec. 6, 2007

(65) Prior Publication Data
US 2010/0048894 A1  Feb. 25, 2010

(30) Foreign Application Priority Data
Jun. 1, 2006 (JP) .................. 2006-153422

(51) Int. Cl.
*A61K 31/495* (2006.01)
(52) U.S. Cl. .......... 514/249; 544/353; 556/19; 556/110
(58) Field of Classification Search .................. 514/249; 544/353; 556/19, 110
See application file for complete search history.

(56) References Cited

U.S. PATENT DOCUMENTS
4,234,729 A  11/1980 Mrowca
5,843,993 A  12/1998 Katti et al.

FOREIGN PATENT DOCUMENTS
JP          61-10594 A   1/1986
JP         10-509957 A   9/1998
JP         2007-56007 A  3/2007
WO         96/17855 A1   6/1996

OTHER PUBLICATIONS

M. J. McKeage, "Antitumor activity of gold (I), silver (I) and copper (I) complexes containing chiral tertiary phosphines", 1998, pp. 217-223, vol. 5, No. 4, Metal-Based Drugs.
T. Imamoto et al., "An Air-Stable p-Chiral Phosphine Ligand for Highly Enantioselective Transition-Metal-Catalyzed Reactions", 2005, pp. 11934-11935, vol. 127, No. 34, Journal of the American Chemical Society.
International Search Report of PCT/JP2007/061046, Mailing Date of Aug. 14, 2007.

*Primary Examiner* — Douglas M Willis
(74) *Attorney, Agent, or Firm* — Westerman, Hattori, Daniels & Adrian, LLP

(57) ABSTRACT

An anticancer agent having a novel chemical structure and high anticancer activity is provided. A phosphine transition metal complex of general formula (1) and an anticancer agent containing the complex are disclosed.

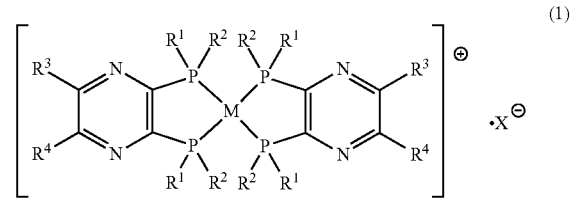

$R^1$ and $R^2$, which may be the same or different, each represent a group having 1 to 10 carbon atoms selected from a straight-chain or branched alkyl group, a cycloalkyl group, a substituted cycloalkyl group, an adamantyl group, a phenyl group, and a substituted phenyl group; $R^3$ and $R^4$, which may be the same or different, each represent a hydrogen atom, a straight-chain alkyl group having 1 to 6 carbon atoms or branched alkyl group having 1 to 6 carbon atoms; or $R^3$ and $R^4$ are taken together to form a saturated or unsaturated ring which may have a substituted group; M represents a transition metal atom selected from the group consisting of gold, copper, and silver; and $X^-$ represents an anion.

6 Claims, No Drawings

PHOSPHINE TRANSITION METAL COMPLEX, PROCESS FOR PRODUCING SAME, AND ANTICANCER AGENT

CROSS-REFERENCE TO RELATED APPLICATIONS

This application is a national stage application under 35 U.S.C. §371 of PCT/JP2007/061046 filed on May 31, 2007, which claims priority under 35 U.S.C. §119(a)-(d) to JP Application No. 2006-153422 filed on Jun. 1, 2006.

FIELD OF THE INVENTION

This invention relates to a novel phosphine transition metal complex, a process for producing the same, and an anticancer agent containing the phosphine transition metal complex.

DESCRIPTION OF RELATED ART

Cisplatin is well known as a substance showing high anticancer activity against cancer cells and has been a mainstay for cancer therapy. Other known high activity anticancer agents include taxol.

It is known from Patent Document 1 and Patent Document 2 that a phosphine transition metal complex having a specific structure exemplified by 1,2-bis(diphenylphosphino)ethane is a compound exhibiting anticancer activity comparable to that of cisplatin.

For example, Patent Documents 1 and 2 propose phosphine transition metal complexes represented by general formula (4) below. In general formula (4) disclosed in Patent Document 1, $R^6$, $R^7$, $R^8$, and $R^9$, which may be the same or different, each represent a group selected from phenyl, substituted phenyl, 4-pyridyl, 3-pyridyl, and 2-pyridyl; A represents —$(CH_2)_n$— or cis-CH=CH—; M' represents gold, silver or copper; and B represents a halogen atom, e.g., chlorine. In general formula (4) disclosed in patent document 2, $R^6$, $R^7$, $R^8$, and $R^9$, which are the same, are selected from phenyl, ethyl, and mono-substituted phenyl; A is —$(CH_2)_n$— or cis-CH=CH—; M' represents gold, silver or copper; and B represents a halogen atom, $PF_6$, or $NO_3$.

[Formula 1]

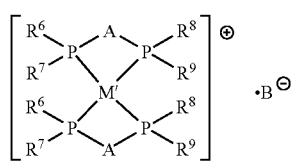

(4)

Patent Document 1 JP 10-509957A
Patent Document 2 JP 61-10594A

It has recently been demanded to develop an anticancer agent having still higher anticancer activity than cisplatin.

The anticancer activity and anticancer spectrum of compounds generally depend on the chemical structure. It is known that the anticancer effect also varies from patient to patient. For example, the efficacy rate of taxol known to have high anticancer activity is even as low as about 30%. Thus, it has been desirable to develop various novel anticancer agents having different chemical structures.

An object of the present invention is to provide an anticancer agent having a novel chemical structure and exhibiting high anticancer activity.

BRIEF SUMMARY OF THE INVENTION

Under these circumstances, the present inventors have conducted extensive studies on novel phosphine transition metal complexes and found as a result that a phosphine transition metal complex having a specific structure shows excellent anticancer activity. The present invention has thus been completed.

The invention (1) provides a phosphine transition metal complex represented by general formula (1):

[Formula 2]

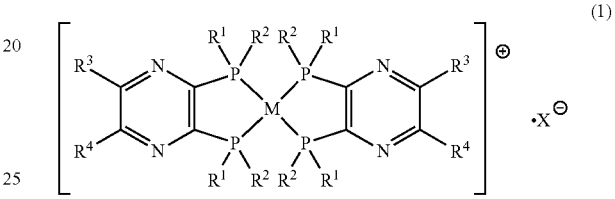

(1)

wherein $R^1$ and $R^2$, which may be the same or different, each represent a group having 1 to 10 carbon atoms selected from a straight-chain or branched alkyl group, a cycloalkyl group, a substituted cycloalkyl group, an adamantyl group, a phenyl group, and a substituted phenyl group; $R^3$ and $R^4$, which may be the same or different, each represent a hydrogen atom, a straight-chain alkyl group having 1 to 6 carbon atoms or branched alkyl group having 1 to 6 carbon atoms; or $R^3$ and $R^4$ are taken together to form a saturated or unsaturated ring which may have a substituted group; M represents a transition metal atom selected from the group consisting of gold, copper, and silver; and $X^-$ represents an anion.

The invention (2) provides a preferred embodiment of the phosphine transition metal complex, in which the complex is represented by general formula (2):

[Formula 3]

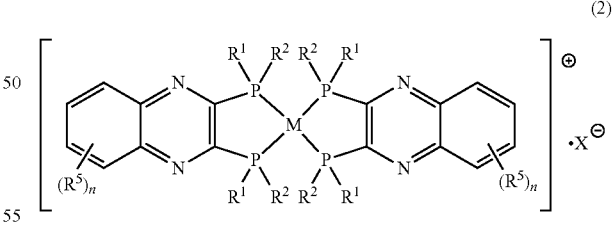

(2)

wherein $R^1$ and $R^2$, which may be the same or different, each represent a group having 1 to 10 carbon atoms selected from a straight-chain or branched alkyl group, a cycloalkyl group, a substituted cycloalkyl group, an adamantyl group, a phenyl group, and a substituted phenyl group; $R^5$ represents a monovalent substituent; n represents an integer of 0 to 4; M represents a transition metal atom selected from the group consisting of gold, copper, and silver; and $X^-$ represents an anion.

The invention (3) provides a still preferred embodiment of the phosphine transition metal complex represented by general formula (1) or (2), wherein $R^1$ is a t-butyl group or an adamantyl group, and $R^2$ is a methyl group.

The invention (4) provides a process which comprises causing a phosphine derivative represented by general formula (3):

[Formula 4]

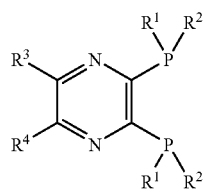

(3)

wherein $R^1$ and $R^2$, which may be the same or different, each represent a group having 1 to 10 carbon atoms selected from a straight-chain or branched alkyl group, a cycloalkyl group, a substituted cycloalkyl group, an adamantyl group, a phenyl group, and a substituted phenyl group; $R^3$ and $R^4$ each represent a hydrogen atom, a straight-chain alkyl group having 1 to 6 carbon atoms or branched alkyl group having 1 to 6 carbon atoms; or $R^3$ and $R^4$ are taken together to form a saturated or unsaturated ring which may have a substituted group, and a salt of a transition metal selected from gold, copper, and silver to react with each other, for producing a phosphine transition metal complex represented by general formula (1):

[Formula 5]

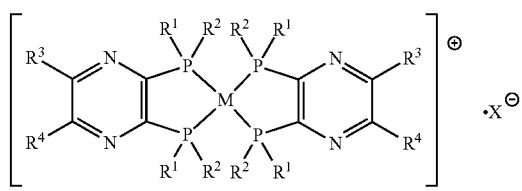

(1)

wherein $R^1$ and $R^2$, which may be the same or different, each represent a group having 1 to 10 carbon atoms selected from a straight-chain or branched alkyl group, a cycloalkyl group, a substituted cycloalkyl group, an adamantyl group, a phenyl group, and a substituted phenyl group; $R^3$ and $R^4$, which may be the same or different, each represent a hydrogen atom, a straight-chain alkyl group having 1 to 6 carbon atoms or branched alkyl group having 1 to 6 carbon atoms; or $R^3$ and $R^4$ are taken together to form a saturated or unsaturated ring which may have a substituted group; M represents a transition metal atom selected from the group consisting of gold, copper, and silver; and $X^-$ represents an anion.

The present invention (5) provides an anticancer agent containing the above-described phosphine transition metal complex of the present invention.

DETAILED DESCRIPTION OF THE INVENTION

The phosphine transition metal complex of the invention is a compound represented by general formula (1).

In general formula (1), $R^1$ and $R^2$ each represent a straight-chain or branched alkyl group, a cycloalkyl group, a substituted cycloalkyl group, an adamantyl group, a phenyl group, or a substituted phenyl group. $R^1$ and $R^2$ each contain 1 to 10 carbon atoms. $R^1$ and $R^2$ may be the same or different.

Examples of the alkyl group as $R^1$ or $R^2$ include methyl, ethyl, isopropyl, n-propyl, isobutyl, n-butyl, sec-butyl, tert-butyl, isoheptyl, n-heptyl, isohexyl, and n-hexyl. Examples of the cycloalkyl group as $R^1$ or $R^2$ include cyclopentyl and cyclohexyl. Examples of the substituent of the substituted cycloalkyl group or the substituted phenyl group as $R^1$ or $R^2$ include alkyl, nitro, amino, hydroxyl, fluoro, chloro, bromo, and iodo. To obtain higher anticancer activity, $R^1$ is preferably a t-butyl group or an adamantyl group, and $R^2$ is preferably a methyl group.

$R^3$ and $R^4$ in general formula (1) each represent a hydrogen atom, a straight-chain alkyl group having 1 to 6 carbon atoms or branched alkyl group having 1 to 6 carbon atoms. $R^3$ and $R^4$ may be the same or different. Alternatively, $R^3$ and $R^4$ are taken together to form a saturated or unsaturated ring, which may have a substituent.

Examples of the alkyl group as $R^3$ or $R^4$ include ethyl, isopropyl, n-propyl, isobutyl, n-butyl, sec-butyl, tert-butyl, isoheptyl, n-heptyl, isohexyl, n-hexyl, cyclopentyl, and cyclohexyl.

When $R^3$ and $R^4$ are taken together to form a saturated or unsaturated ring, the ring is exemplified by a saturated or unsaturated 5-membered ring or a saturated or unsaturated 6-membered ring, such as phenyl, cyclohexyl, or cyclopentyl. The ring formed by $R^3$ and $R^4$ taken together may have a monovalent substituent. Examples of the substituent include a straight-chain alkyl group having 1 to 5 carbon atoms or branched alkyl group having 1 to 5 carbon atoms, a nitro group, an amino group, a hydroxyl group, a fluoro group, a chloro group, a bromo group, and an iodo group.

In general formula (1), M represents a transition metal atom selected from the group consisting of gold, copper, and silver. To obtain higher anticancer activity, M is preferably a gold atom.

In general formula (1), $X^-$ represents an anion. Examples of the anion include a chloride ion, a bromide ion, an iodide ion, a tetrafluoroborate ion, a hexafluorophosphate ion, and a perchlorate ion. To obtain higher anticancer activity, $X^-$ is preferably a chloride, bromide or iodide ion.

To obtain higher anticancer activity, it is preferred that $R^3$ and $R^4$ in general formula (1) are taken together to form a benzene ring.

The phosphine transition metal complex in which $R^3$ and $R^4$ are taken together to form a benzene ring is a phosphine transition metal complex represented by general formula (2).

In general formula (2), $R^1$, $R^2$, M, and $X^-$ are as defined in general formula (1).

In general formula (2), $R^5$ represents a monovalent substituent exemplified by a straight-chain alkyl group having 1 to 5 carbon atoms or branched alkyl group having 1 to 5 carbon atoms, a nitro group, an amino group, a hydroxyl group, a fluoro group, a chloro group, a bromo group, or an iodo group; and n represents an integer of 0 to 4.

The phosphine transition metal complex of general formula (1) in which $R^1$ and $R^2$ are different groups is a phosphine transition metal complex as represented by general formula (5):

[Formula 6]

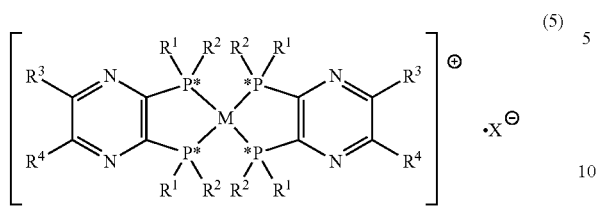

(5)

The phosphine transition metal complex has an asymmetric center on its phosphorus atoms.

In general formula (5), $R^1$, $R^2$, $R^3$, $R^4$, M, and $X^-$ are as defined in general formula (1); and the asterisk mark * indicates an asymmetric phosphorus atom.

Having four asymmetric phosphorus atoms, the phosphine transition metal complex of general formula (5) takes on many isomeric configurations. The compound of general formula (5) is not limited by such isomeric configuration. More specifically, the steric configuration on the phosphorus atoms may be a single enantiomer, such as an (R,R)(R,R) configuration or an (S,S)(S,S) configuration; a racemic configuration, such as an (R,R)(S,S) configuration; a meso form, such as an (R,S)(S,R) configuration; or a mixture of an enantiomer and its meso form, such as an (R,R)(S,R) configuration.

The phosphine transition metal complex represented by general formula (1) is prepared by causing a phosphine derivative represented by general formula (3) and a salt of a transition metal selected from gold, copper, and silver to react with each other.

The process for producing a phosphine transition metal complex according as contemplated in the present invention is a process for producing the phosphine transition metal complex represented by general formula (1), which comprises causing the phosphine derivative represented by general formula (3) and a salt of a transition metal selected from gold, copper, and silver to react with each other.

$R^1$, $R^2$, $R^3$, and $R^4$ in general formula (3) are as defined in general formula (1). That is, $R^1$, $R^2$, $R^3$, and $R^4$ in general formula (3) are equivalent to $R^1$, $R^2$, $R^3$, and $R^4$ in general formula (1), respectively.

The phosphine derivative of general formula (3) is prepared by, for example, causing a 2,3-dichloroquinoxaline (6) and a phosphine-borane (7) to react with each other to obtain a bis(phosphine-borane)quinoxaline (8), which is then subjected to deboranation reaction as illustrated in reaction scheme (9) shown below.

[Formula 7]

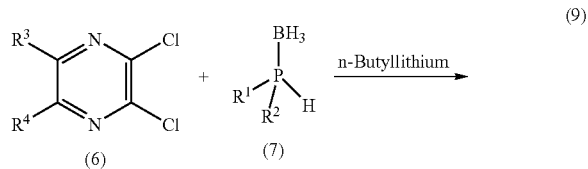

(9)

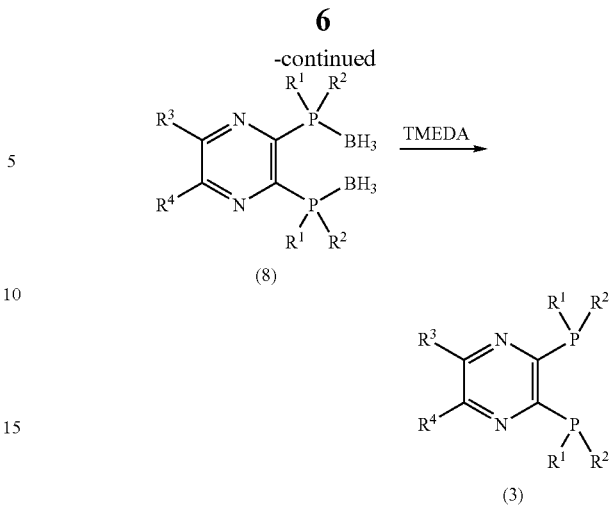

In reaction scheme (9), the reaction between the 2,3-dichloroquinoxaline (6) and the phosphine-borane (7) is carried out, for example, in an inert solvent, e.g., tetrahydrofuran, in the presence of a base, e.g., n-butyllithium, at −78° C. to 30° C. for 1 to 24 hours.

The 2,3-dichloroquinoxaline (6) and the phosphine-borane (7) are prepared by known processes. The 2,3-dichloroquinoxaline (6) is commercially available. The phosphine-borane (7) is prepared by, for example, the processes described in JP 2003-300988A, JP 2001-253889A, and *J. Org. Chem.*, vol. 65, pp. 4185-4188 (2000).

Deboranation of the bis(phosphine-borane)quinoxaline (8) is achieved by adding a deboranating agent, such as N,N,N',N'-tetramethylethylenediamine (TMEDA), to the reaction system containing the bis(phosphine-borane)quinoxaline (8) and causing them to react at 0° C. to 100° C. for 10 minutes to 3 hours.

The transition metal salt that can be used in the preparation of the phosphine transition metal complex of the invention is a salt between a gold ion, a copper ion, or a silver ion and an anion. Examples of the transition metal salt include a halide, a nitrate, a perchlorate, a tetrafluoroborate, and a hexafluorophosphate of gold, copper or silver. The valence of the transition metal ion in the gold, copper or silver salts is monovalent. One or both of the transition metal and the anion making the gold, copper or silver salt may be composed of two or more species.

Exemplary and preferred gold salts are chloroauric acid, gold (I) chloride, and tetrabutylammonium chloride-gold (I) chloride (see The Chemical Society of Japan (ed.), *Jikken Kagaku Koza* 21, 5th Ed., Maruzen, pp. 366-380, Mar. 30, 2004, and *Aust. J. Chemm.*, No. 50, pp. 775-778, 1997). Exemplary and preferred copper salts are copper (I) chloride, copper (I) bromide, and copper (I) iodide (see The Chemical Society of Japan (ed.), *Jikken Kagaku Koza* 21, 5th Ed., Maruzen, pp. 349-361, Mar. 30, 2004). Exemplary and preferred silver salts are silver (I) chloride, silver (I) bromide, and silver (I) iodide (see he Chemical Society of Japan (ed.), *Jikken Kagaku Koza* 21, 5th Ed., Maruzen, pp. 361-366, Mar. 30, 2004). The transition metal salt to be used in the preparation of the phosphine transition metal complex of the invention may be either anhydrous or in a hydrated state.

The gold, copper or silver transition metal salt and 1 to 5 times, preferably 1.8 to 2.2 times, the molar quantity of the phosphine derivative of general formula (3) are allowed to react in a solvent, such as acetone, acetonitrile, methanol, or ethanol, at a reaction temperature of −20° C. to 60° C., preferably 0° C. to 25° C., for a period of 0.5 to 48 hours, preferably 1 to 3 hours, to yield the phosphine transition metal complex of general formula (1). After completion of the reaction, the reaction product is purified in a usual manner according to necessity.

The anion of the phosphine transition metal complex of general formula (1) as obtained by the process according to the present invention can be exchanged with a desired anion to afford another phosphine transition metal complex of general formula (1) having the desired anion. This can be achieved, for example, as follows.

A phosphine transition metal complex of general formula (1) in which $X^-$ is a halide ion is synthesized in accordance with the above described process of the present invention. The resulting phosphine transition metal complex ($X^-$: halide ion) is then caused to react with an organic or inorganic acid having a desired anion or an alkali metal salt thereof in an appropriate solvent to give a phosphine transition metal complex in which $X^-$ is the desired anion. Reference can be made to JP 10-147590A, JP 10-114782A, and JP 61-10594A.

The phosphine transition metal complex which is optically active is obtained by starting with an optically active phosphine-borane (7) in reaction scheme (9) supra to synthesize an optically active phosphine derivative represented by general formula (3), which is then caused to react with a gold, copper or silver salt. The optically active phosphine-borane (7) is prepared by, for example, the processes described in JP 2001-253889A, JP 2003-300988A, and *J. Org. Chem.*, vol. 65, pp. 4185-4188, 2000. Starting with a phosphine-borane (7) in which $R^1$ and $R^2$ are different results in the production of a phosphine transition metal complex of general formula (5).

The phosphine transition metal complex of the invention exhibits high anticancer activity as will be described and is therefore useful as an anticancer agent.

The anticancer agent according to the invention contains at least one phosphine transition metal complex represented by general formula (1).

As previously stated, of the phosphine transition metal complexes of general formula (1), those having an asymmetric center on the phosphorus atoms, namely, the phosphine transition metal complexes of general formula (5) embrace a number of isomers. The anticancer agent of the invention may contain one or more than one of the isomers.

The type of the cancers that can be treated with the anticancer agent of the invention are not particularly limited and include malignant melanoma, malignant lymphoma, gastrointestinal carcinoma, lung carcinoma, esophageal carcinoma, gastric carcinoma, large bowel cancer, rectal carcinoma, colon carcinoma, ureteral tumor, gallbladder carcinoma, cholangiocarcinoma, biliary tract carcinoma, breast carcinoma, heptatocarcinoma, pancreas carcinoma, testicular tumor, maxillary carcinoma, tongue carcinoma, lip carcinoma, oral carcinoma, pharyngeal carcinoma, laryngeal carcinoma, ovarian carcinoma, uterine carcinoma, prostatic carcinoma, thyroid carcinoma, brain tumor, Kaposi's sarcoma, hemangioma, leukemia, polycythemia vera, neuroblastoma, retinoblastoma, myeloma, bladder tumor, sarcoma, osteosarcoma, myosarcoma, skin carcinoma, basal cell carcinoma, skin appendage carcinoma, metastatic skin cancer, and cutaneous melanoma. The anticancer agent is useful to treat benign tumors as well as malignant tumors. The anticancer agent of the invention is also useful to inhibit cancer metastasis. It is particularly useful as a cancer metastasis suppressor after surgery.

In the use of the anticancer agent of the invention, the anticancer agent of the invention may be administered to humans or animals through various routes. It is administered either orally or parenterally (for example, intravenously, intramuscularly, subcutaneously, intracutaneously, intrarectally, or transmucousally). Dosage forms suitable for oral administration include tablets, pills, granules, powders, capsules, liquids, suspensions, emulsions, and syrups. Pharmaceutical compositions suitable for parenteral administration includes injections, drops, nose drops, sprays, inhalations, suppositories, and percutaneous absorptive preparations, such as ointments, creams, powdery liniments, liquid liniments, and patches. The anticancer agent of the invention may also be formulated into sustained-release preparations, such as implantable pellets, by known techniques.

A suitable administration route, dosage form, and the like are decided by a doctor as appropriate to the age, sex, constitution, symptoms, and timing of treatment of a patient, and the like.

The anticancer agent in the form of solid preparations, such as tablets, pills, powders, or granules is prepared by mixing the phosphine transition metal complex of general formula (1) with appropriate additives in a customary manner. Examples of the additive include vehicles, such as lactose, sucrose, D-mannitol, corn starch, synthetic or natural gum, and crystalline cellulose; binders, such as starch, hydroxypropyl cellulose, hydroxypropylmethyl cellulose, gum arabic, gelatin, and polyvinylpyrrolidone; disintegrators, such as calcium carboxymethyl cellulose, sodium carboxymethyl cellulose, starch, corn starch, and sodium alginate; lubricants, such as talc, magnesium stearate, and sodium stearate; and bulking agents or diluents, such as calcium carbonate, sodium carbonate, calcium phosphate, and sodium phosphate. Where necessary, tablets and the like may be subjected to sugar coating, gelatin coating, enteric coating, or film coating with a coating agent, such as hydroxypropylmethyl cellulose, sucrose, polyethylene glycol, or titanium oxide.

The anticancer agent in the form of liquid preparations, such as an injection, an eye drop, a nose drop, an inhalation, a spray, a lotion, a syrup, a solution, a suspension, or an emulsion is prepared by dissolving the phosphine transition metal complex of general formula (1) in an appropriate solvent, such as purified water, a buffer solution (e.g., a phosphate buffer solution), a physiological salt solution (e.g., physiological saline, a Ringer's solution, or a Locke's solution), a vegetable oil (e.g., cacao butter, sesame oil, or olive oil), a mineral oil, or an organic solvent (e.g., a higher alcohol, a higher fatty acid, or ethanol). Where needed, the resulting mixture may further contain an emulsifier (e.g., cholesterol), a suspending agent (e.g., gum arabic), a dispersing aid, a wetting agent, a surface active agent (e.g., polyoxyethylene hydrogenated castor oil or polyethylene glycol), a solubilizer (e.g., sodium phosphate), a stabilizer (e.g., sugar, a sugar alcohol, or albumin), a preservative (e.g., paraben), a tonicity agent (e.g., sodium chloride, glucose, or glycerol), a buffer, a soothing agent, an adsorption prevention agent, a humectant, an antioxidant, a coloring agent, a sweetener, a flavor, an aromatic substance, and so on. The anticancer agent is thus supplied in the form of a sterile aqueous solution, nonaqueous solution, suspension, ribosome, or emulsion or the like. The injections are preferably adjusted to have a physiological pH, more preferably in the range of from 6 to 8.

The anticancer agent of the invention in the form of semi-solid preparations, such as lotions, creams, and ointments, can be prepared by mixing the phosphine transition metal complex appropriately with fat, fatty oil, lanolin, petrolatum, paraffin, wax, plaster, a resin, plastic, a glycol, a higher alcohol, glycerol, water, an emulsifier, a suspending agent, and so forth.

The content of the phosphine transition metal complex of general formula (1) in the anticancer agent of the invention varies depending on a dosage form, severity, a target dose, and the like. In general, the content is 0.001% to 80% by weight, preferably 0.1% to 50% by weight, relative to the total weight of the anticancer agent.

The dose of the anticancer agent of the invention is appropriately determined by a doctor according to, for example, the age, sex, body weight, and symptoms of a patient, and the administration route. In general, the active ingredient is administered in a dose of about 1 μg/kg to 1,000 mg/kg, preferably about 10 μg/kg to 10 mg/kg, per day for an adult. The above-described dose of the anticancer agent may be administered in single or divided doses (e.g., about 2 to 4 times) per day.

The anticancer agent of the invention may be used in combination with known chemotherapy, surgical treatment, radiation therapy, thermotherapy, immunotherapy, or the like.

Because the phosphine transition metal complex of general formula (1) has higher water solubility than those proposed in patent documents 1 and 2 supra, it effectively acts as an anticancer agent on an affected part at a smaller dose regardless of an administration route or dosage form and therefore has an advantage of a reduced dose.

The present invention will now be illustrated in greater detail by way of Examples, but it should be understood that the invention is not construed as being limited thereto.

EXAMPLES

Synthesis Example 1

(1) Synthesis of t-butylmethylphosphine-borane (7a)

t-Butylmethylphosphine-borane (7a) was synthesized in accordance with reaction scheme (11):

[Formula 8]

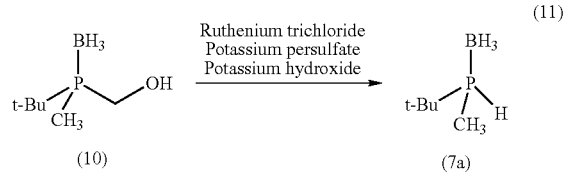

In 72 ml of acetone was dissolved 1.78 g (12.0 mmol) of t-butyl(hydroxymethyl)methylphosphine-borane (10). Separately, 13.5 g (240 mmol) of potassium hydroxide, 19.4 g (72.0 mmol) of potassium persulfate, and 624 mg (2.4 mmol) of ruthenium trichloride trihydrate were dissolved in 150 ml of water. The resulting aqueous solution was vigorously stirred, and the acetone solution prepared above was slowly added thereto at 0° C. Two hours later, the reaction mixture was neutralized with 3M hydrochloric acid and extracted three times with ether. The organic phase was washed with a saturated sodium chloride aqueous solution and dried over sodium sulfate. The solvent was removed on a rotary evaporator at room temperature. The residue was purified by silica gel column chromatography (mobile phase: pentane/ether=8/1) to yield 2.27 g (80%) of t-butylmethylphosphine-borane (7a).

(2) Synthesis of 2,3-bis(t-butylmethylphosphino)quinoxaline (3a)

2,3-Bis(t-butylmethylphosphino)quinoxaline (3a) was synthesized in accordance with reaction scheme (12):

[Formula 9]

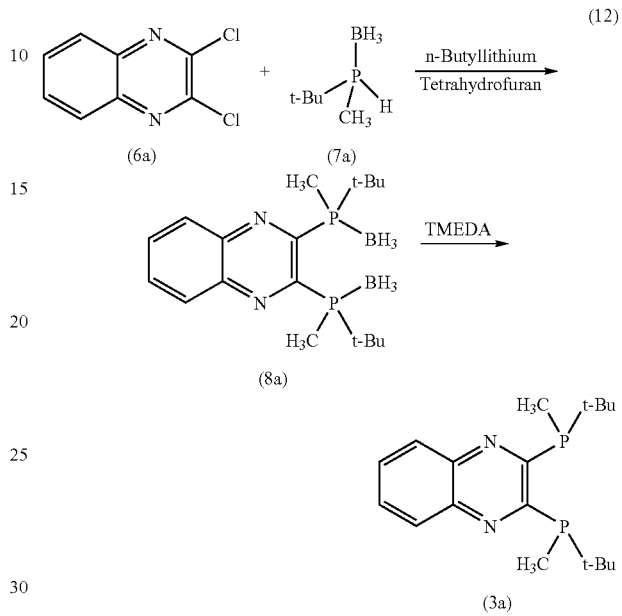

In 4 ml of tetrahydrofuran was dissolved 236 mg (2.0 mmol) of t-butylmethylphosphine-borane (7a). The solution was cooled to −78° C. with liquid nitrogen. To the cooled solution was added dropwise 1.25 ml of a 1.6M hexane solution of n-butyllithium. After 15 minutes, a solution of 133 mg (0.67 mmol) of 2,3-dichloroquinoxaline (6a) (from Kanto Chemical Co., Inc.) in 4 ml of tetrahydrofuran was added thereto while vigorously stirring. The mixture was warmed to room temperature (25° C.) over a period of 1 hour and stirred at that temperature for 3 hours. One milliliter of TMEDA was added thereto, and the stirring was continued for an addition 2 hour period. The reaction was stopped by the addition of 1M hydrochloric acid. The reaction mixture was extracted with hexane, and the organic phase was washed successively with 1M hydrochloric acid and a saturated sodium chloride aqueous solution and dried over sodium sulfate. The solvent was removed by vacuum suction, and the residue was purified by silica gel column chromatography (mobile phase: hexane/ethyl acetate=30/1) to give an orange solid. Recrystallization of the solid with 1.7 ml of hot methanol afforded 2,3-bis(t-butylmethylphosphino)-quinoxaline (3a) as orange crystals in a yield of 80%. The physical properties of the resulting 2,3-bis(t-butylmethylphosphino)quinoxaline (3a) were as follows.

Identification Data:
$^1$H-NMR (395.75 MHz, CDCl$_3$): β 1.00-1.03 (m, 18H), 1.42-1.44 (m, 6H), 7.70-7.74 (m, 2H,), 8.08-8.12 (m, 2H)
$^{13}$C-NMR (99.45 MHz, CDCl$_3$): β 4.77 (t, J=4.1 Hz), 27.59 (t, J=7.4 Hz), 31.90 (t, J=7.4 Hz), 129.50, 129.60, 141.63, 165.12 (dd, J=5.7, 2.4 Hz)
$^{31}$P-NMR (202.35 MHz, CDCl$_3$): β −17.7(s)
IR (KBR): 2950, 1470, 780 cm$^{-1}$
HRMS (FAB): calculated for C$_{18}$H$_{29}$N$_2$P$_2$ (M$^+$+H): 335.1809; found: 335.1826

Example 1

Synthesis of bis(2,3-bis(t-butylmethylphosphino)quinoxaline)gold (I) chloride (1a)

In a 25 ml two-necked flask purged with nitrogen were put 1.33 g (3.98 mmol) of 2,3-bis(t-butylmethylphosphino)quinoxaline (3a) and degassed THF. To the mixture was added 1.02 mg (1.99 mmol) of tetrabutylammoniumgold (I) dichloride, followed by stirring at room temperature for 20 hours. The precipitate was separated, and the filtrate was concentrated to dryness. The resulting brown solid was dried under reduced pressure to give 1.46 g (82%) of bis(2,3-bis(t-butylmethylphosphino)-quinoxaline)gold (I) chloride of general formula (1a).

[Formula 10]

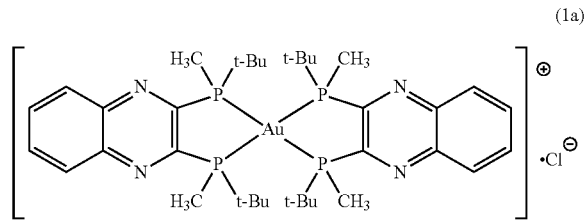

Identification Data:
$^{31}$P-NMR (121.55 MHz, CDCl$_3$): 8.8 (s)
MS (ESI, POS) m/z: 866 (M$^+$–Cl$^-$)

Evaluation of Anticancer Activity

The resulting bis(2,3-bis(t-butylmethylphosphino)quinoxaline)gold (I) chloride (1a) was tested to evaluate inhibitory activity on tumor cells as follows. For comparison, cisplatin (Comparative Example 1) was tested in the same manner.

Human acute myelocytic leukemia cells HL-60 was used as cancer cells. The cells were cultured in Rosewell Park Memorial Institute medium (RPMI 1640) supplemented with 10% fetal bovine serum, 1% antibiotic, and an antifungal agent in a humidified 5% CO$_2$ incubator at 37° C.

The cells were washed with PBS. After the number of the cells was determined, the cells were suspended in the same medium to prepare a suspension containing 1×10$^6$ cells/ml. The cell suspension was seeded to a sterile 96-well microplate at 50,000 cells/well.

A phosphine transition metal complex solution (Example 1) prepared by completely dissolving the bis(2,3-bis(t-butylmethylphosphino)quinoxaline)gold (I) chloride (1a) in water or a cisplatin solution (Comparative Example 1) prepared by completely dissolving cisplatin in dimethyl sulfoxide was added to each well. The cells were further cultured in the incubator for 24 hours.

The number of viable cells was determined by a modified Mosmann method (T. Mosmann, *J. Immunnol. Method*, 65, pp. 55-63, 1983). That is, a solution of a tetrazolium salt (3-[4,5-dimethylthiazole-2-yl]-2,5-diphenyltetrazolium bromide, MTT) was added thereto, and the culturing was continued under the same conditions for an additional 3 hour period. Formazan crystals formed by the enzyme activity of mitochondria in the cells were dissolved in 0.04 mol/HCl/isopropyl alcohol. The absorbance of each well was read at 595 nm and 630 nm with a microplate reader (Bio-Rad 550). The latter reading (background) was subtracted from the former reading to give the number of viable cells. Fifty percent inhibitory concentration (IC$_{50}$) was then calculated. The test was run in at least triplicate to obtain an average. The results obtained are shown in Table 1 below.

TABLE 1

| | IC$_{50}$ (μM/L) |
|---|---|
| Example 1 | 0.517 |
| Comparative Example 1 | 23.6 |

As is apparent from the results in Table 1, bis(2,3-bis(t-butylmethylphosphino)-quinoxaline)gold (I) chloride (1a) has higher anticancer activity than cisplatin.

Example 2

Fifty grams of bis(2,3-bis(t-butylmethylphosphino)quinoxaline) gold (I) chloride (1a) obtained in the same manner as in Example 1, 400 g of lactose, and 50 g of corn starch were mixed in a blender to make a powder.

Example 3

Fifty grams of bis(2,3-bis(t-butylmethylphosphino)quinoxaline) gold (I) chloride (1a) obtained in the same manner as in Example 1, 250 g of lactose, and 50 g of low-substituted hydroxypropyl cellulose were mixed. To the mixture was added 150 g of a 10% aqueous solution of hydroxypropyl cellulose, followed by kneading. The mixture was granulated in an extruding granulator to form granules.

Example 4

Fifty grams of bis(2,3-bis(t-butylmethylphosphino)quinoxaline) gold (I) chloride (1a) obtained in the same manner as in Example 1, 250 g of lactose, 120 g of corn starch, 75 g of crystalline cellulose, and 5 g of magnesium stearate were mixed in a blender. The mixture was compressed by a tabletting machine to form tablets.

Example 5

Twenty-five grams of bis(2,3-bis(t-butylmethylphosphino)quinoxaline) gold (I) chloride (11a) obtained in the same manner as in Example 1, 300 g of lactose, 170 g of corn starch, and 5 g of magnesium stearate were mixed in a V-blender. The mixture was introduced in 180 mg portions in capsules of size 3 to make capsules.

Example 6

A hundred milligrams of bis(2,3-bis(t-butylmethylphosphino)quinoxaline) gold (I) chloride (1a) obtained in the same manner as in Example 1 and 100 mg of glucose were dissolved in 2 ml of purified water, followed by filtration. The filtrate was dispensed into 2 ml ampoules. The ampoules were sealed and sterilized to make injections.

Example 7

One gram of bis(2,3-bis(t-butylmethylphosphino)quinoxaline) gold (I) chloride (1a) obtained in the same manner as in Example 1, 3 g of ethanol, 0.2 g of hydroxyethyl cellulose, and 0.1 g of methyl p-hydroxybenzoate were dissolved in 100 ml of purified water to form a lotion.

Example 8

Two grams of bis(2,3-bis(t-butylmethylphosphino)quinoxaline) gold (I) chloride (1a) obtained in the same manner as in Example 1, 6 g of liquid paraffin, 2 g of beeswax, 3 g of self-emulsifying glyceryl monostearate, and 5 g of white petrolatum were heated to melt and disperse, thereby to form an ointment.

Example 9

Two grams of bis(2,3-bis(t-butylmethylphosphino)quinoxaline) gold (I) chloride (1a) obtained in the same manner as in Example 1 was dispersed in a mixture of 2 g of glyceryl monostearate, 4 g of stearyl alcohol, 2 g of octyldodecanol, and 5 g of polyoxyethylene sorbitan monooleate under heat. A solution prepared by dissolving 0.1 g of methyl p-hydroxybenzoate and 5 g of glycerol in 60 g of purified water under heat was added thereto. The resulting mixture was emulsified by high-speed stirring and cooled to form a cream.

Industrial Applicability

The present invention provides an anticancer agent having a novel chemical structure and high anticancer activity. The invention also provides an industrially advantageous process for producing a phosphine transition metal complex represented by general formula (1).

The invention claimed is:
1. A phosphine transition metal complex represented by formula (1):

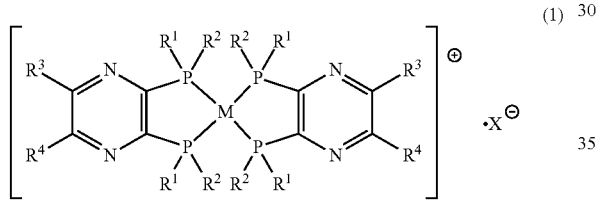

wherein
$R^1$ and $R^2$, which are the same or different, each represent a group having 1 to 10 carbon atoms selected from a straight-chain or branched alkyl group, a cycloalkyl group, a substituted cycloalkyl group, an adamantyl group, a phenyl group, and a substituted phenyl group, wherein a substituent of the substituted cycloalkyl group or the substituted phenyl group as $R^1$ or $R^2$ is selected from the group consisting of alkyl, nitro, amino, hydroxy, fluoro, chloro, bromo or iodo;
$R^3$ and $R^4$ taken together represent a benzene ring with or without a substituted group, wherein the substituted group is selected from the group consisting of a straight-chain alkyl group having 1 to 5 carbon atoms, a branched alkyl group having 1 to 5 carbon atoms, a nitro group, an amino group, a hydroxy group, a fluoro group, a chloro group, a bromo group, and an iodo group;
M is gold; and
$X^-$ represents an anion, wherein the anion is selected from the group consisting of chloride ion, bromide ion, iodide ion, tetrafluoroborate ion, hexafluorophosphate ion, and perchlorate ion.
2. The phosphine transition metal complex according to claim 1, wherein $R^1$ is a t-butyl group or an adamantyl group, and $R^2$ is a methyl group.
3. A pharmaceutical composition comprising a pharmaceutically acceptable carrier and a phosphine transition metal complex represented by formula (1):

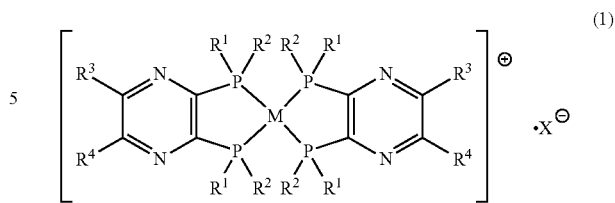

wherein
$R^1$ and $R^2$, which are the same or different, each represent a group having 1 to 10 carbon atoms selected from a straight-chain or branched alkyl group, a cycloalkyl group, a substituted cycloalkyl group, an adamantyl group, a phenyl group, and a substituted phenyl group, wherein a substituent of the substituted cycloalkyl group or the substituted phenyl group as $R^1$ or $R^2$ is selected from the group consisting of alkyl, nitro, amino, hydroxyl, fluoro, chloro, bromo or iodo;
$R^3$ and $R^4$ taken together represent a benzene ring with or without a substituted group, wherein the substituted group is selected from the group consisting of a straight-chain alkyl group having 1 to 5 carbon atoms, a branched alkyl group having 1 to 5 carbon atoms, a nitro group, an amino group, a hydroxy group, a fluoro group, a chloro group, a bromo group, and an iodo group;
M is gold; and
$X^-$ represents an anion, wherein the anion is selected from the group consisting of chloride ion, bromide ion, iodide ion, tetrafluoroborate ion, hexafluorophosphate ion, and perchlorate ion.
4. The pharmaceutical composition comprising a pharmaceutically acceptable carrier and a phosphine transition metal complex according to claim 3, wherein $R^1$ is a t-butyl group or an adamantyl group, and $R^2$ is a methyl group.
5. A phosphine transition metal complex, which is represented by formula (2):

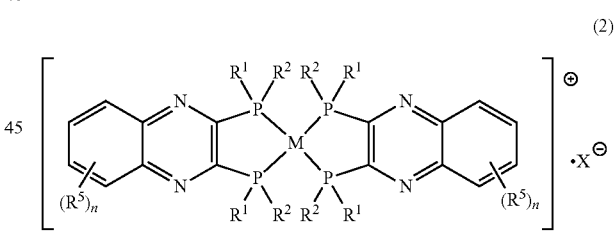

wherein
$R^1$ and $R^2$, which are the same or different, each represent a group having 1 to 10 carbon atoms selected from a straight-chain or branched alkyl group, a cycloalkyl group, a substituted cycloalkyl group, an adamantyl group, a phenyl group, and a substituted phenyl group, wherein a substituent of the substituted cycloalkyl group or the substituted phenyl group as $R^1$ or $R^2$ is selected from the group consisting of alkyl, nitro, amino, hydroxyl, fluoro, chloro, bromo or iodo;
$R^5$ represents a monovalent substituent; n represents an integer of 0, 1, 2, 3 or 4, wherein the monovalent substituent is selected from the group consisting of a straight-chain alkyl group having 1 to 5 carbon atoms, a branched alkyl group having 1 to 5 carbon atoms, a nitro group, an amino group, a hydroxy group, a fluoro group, a chloro group, a bromo group, or an iodo group;

M is gold; and

X⁻ represents an anion, wherein the anion is selected from the group consisting of chloride ion, bromide ion, iodide ion, tetrafluoroborate ion, hexafluorophosphate ion, and perchlorate ion.

6. The phosphine transition metal complex according to claim 5, wherein $R^1$ is a t-butyl group or an adamantyl group, and $R^2$ is a methyl group.

* * * * *